United States Patent [19]

Shimizu et al.

[11] Patent Number: 4,595,021
[45] Date of Patent: Jun. 17, 1986

[54] BLOOD COLLECTOR

[75] Inventors: Atsushi Shimizu; Toshiji Ichikawa, both of Tokyo, Japan

[73] Assignee: Terumo Corporation, Tokyo, Japan

[21] Appl. No.: 741,036

[22] Filed: Jun. 4, 1985

Related U.S. Application Data

[63] Continuation of Ser. No. 465,348, Feb. 9, 1983, abandoned.

[30] Foreign Application Priority Data

Feb. 15, 1982 [JP] Japan .................................. 57-22431

[51] Int. Cl.[4] .............................................. A61B 5/14
[52] U.S. Cl. ...................................... 128/760; 604/266
[58] Field of Search ........................ 128/760, 763–765; 604/52, 126, 190, 266

[56] References Cited

U.S. PATENT DOCUMENTS

| | | | |
|---|---|---|---|
| 4,257,426 | 3/1981 | Bailey | 128/766 |
| 4,340,067 | 7/1982 | Rattenborg | 128/763 |
| 4,361,155 | 11/1982 | Anastasio | 128/765 X |
| 4,373,535 | 2/1983 | Martell | 128/765 |
| 4,385,637 | 5/1983 | Akhavi | 128/763 |
| 4,398,544 | 8/1983 | Nugent et al. | 128/763 |
| 4,416,291 | 11/1983 | Kaufman | 128/763 X |

Primary Examiner—Kyle L. Howell
Assistant Examiner—Angela D. Sykes
Attorney, Agent, or Firm—Frishauf, Holtz, Goodman & Woodward

[57] ABSTRACT

A blood collector includes a cylindrical body having a closed end and an open end, and a hollow body is arranged coaxially at the closed end of the cylindrical body and has a hole communicating with the interior of the cylindrical body. A columnar body is arranged within the cylindrical body to be in tight contact with an inner wall thereof, with a distal end defining a blood collection space with the closed end of the cylindrical body. Further, the columnar body has a hole which allows the blood collection space to communicate with the outside. A freeze-dried blood anticoagulant mass is placed inside the blood collection space to cover an inner surface of the closed end of the cylindrical body and to block the hole of the hollow body. A filter is arranged across the hole of the columnar body. The filter is permeable to gases and impermeable to blood at least before being brought into contact with blood in the collection space.

14 Claims, 7 Drawing Figures

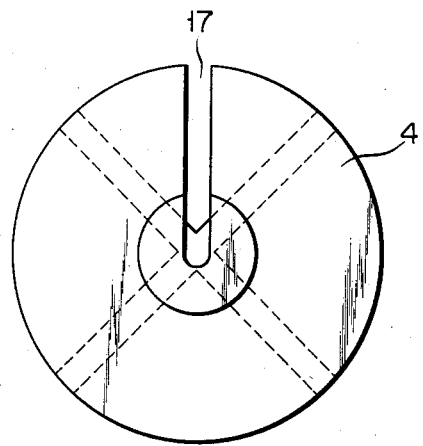
F I G. 6
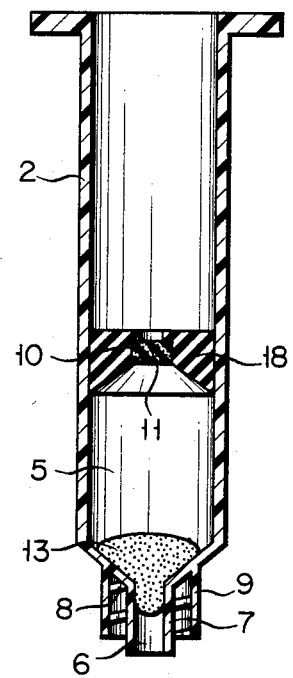
F I G. 7

BLOOD COLLECTOR

This application is a continuation of application Ser. No. 465,348, filed Feb. 9, 1983, now abandoned.

BACKGROUND OF THE INVENTION

I. Field of the Invention

The present invention relates to an instrument for collecting blood, particularly, arterial blood.

II. Description of the Prior Art

In order to examine the pulmonary functioning and acid-base balance of a human body, blood tests called blood gas analysis are performed. Such tests include measurement of the dissolved oxygen and carbon dioxide content of arterial blood; measurement of the oxygen saturation or the pH of arterial blood; and quantitative analysis of the blood content of electrolytes such as $HCO_3^-$, $Na^+$, $K^+$, or $Cl^-$.

In such blood gas analysis, if air is introduced into a blood sample to be tested, measurement precision is adversely affected. Therefore, air must not be introduced into the blood sample after collection.

For this purpose, it has been proposed to collect blood after drawing a heparin solution into a blood collection space of a blood collector, or to use a blood collection container in which a heparin solution is pre-filled (Japanese Utility Model Nos. 53-49268, 52-42064). When such measures are taken, the dead space in the blood collection container and in a blood collection cannula is filled with the heparin solution to prevent any air from remaining therein. A heparin solution which may be generally used has a heparin concentration of about 1,000 units/ml. A diluent may be water, physiological saline solution or the like. The heparin solution thus prepared is mixed with the collected blood to dilute it. However, the results of blood gas analysis vary, due to variations in the degree of dilution of blood by the heparin solution, so that correct blood gas measurements may not be performed.

In view of this, it has also been proposed in U.S. Pat. No. 4,257,426 to introduce dry heparin as an anticoagulant into a blood collection space so that the problem of variations in the degree of dilution of blood by the heparin solution may be prevented, and to incorporate a separate mechanism in the blood collector for removing air and for providing an air-tight seal between the blood and ambient air. The above patent discloses a blood collector in which a dry heparin mass is placed in a blood collection space thereof. However, depending on the tilt angle of the blood collector, the heparin mass may not be situated in the vicinity of the blood inlet port at the closed end of an outer cylinder. Therefore, if blood pressure is high, initially introduced blood may not be brought into contact with the heparin mass, so that the heparin mass may not serve its original purpose. In this case, air becomes trapped between the hub and the outer cylinder.

SUMMARY OF THE INVENTION

It is an object of the present invention to provide a blood collector which eliminates the drawbacks of the prior art, which is capable of suppressing the effect of high blood pressure in a patient, and which allows blood collection without allowing air to remain between its hub and outer cylinder or container.

In order to achieve the above object, there is provided according to the present invention a blood collector comprising:

a cylindrical body having a closed end and an open end;

a hollow body which is arranged at the closed end of said cylindrical body and which has a hole communicating with an interior of said cylindrical body;

a columnar body which is arranged within said cylindrical body to be in tight contact with an inner wall thereof, and a distal end of which defines a blood collection space together with the closed end of said cylindrical body, said columnar body having a hole which allows said blood collection space to communicate with the outside atmosphere;

a freeze-dried blood anticoagulant mass which is placed inside said blood collection space to cover an inner surface of the closed end of said cylindrical body and to block the hole of said hollow body; and a filter which is arranged to laterally cross the entire hole of said columnar body, said filter being permeable to gases and impermeable to blood at least before being brought into contact with blood.

In accordance with an aspect of the present invention, the blood coagulant is a heparin salt. The freeze-dried heparin salt mass partially extends into the hole of the hollow body to be fixed thereto with considerable strength.

In accordance with another aspect of the present invention, the filter has a water-induced swelling property. When the filter is brought into contact with sampled blood in the blood collection space, it swells to close the hole of the columnar body so that blood may not flow therethrough.

BRIEF DESCRIPTION OF THE DRAWINGS

FIG. 6 is a forward side view of the plunger shown in FIG. 5; and

FIG. 7 is a sectional view of a blood collector according to another embodiment of the present invention.

DETAILED DESCRIPTION OF THE PREFERRED EMBODIMENTS

Figures 1, 2:
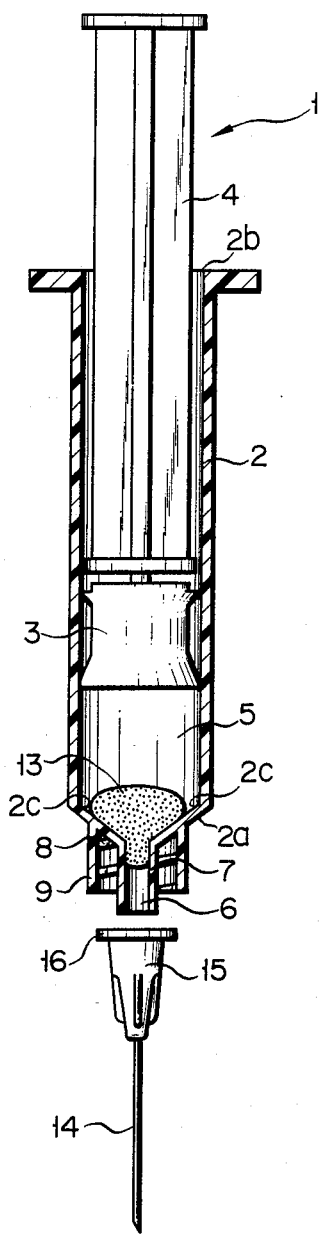
FIG. 1 is a partially sectional side view of a blood collector according to an embodiment of the present invention.
FIG. 2 is a side view of a hub with a blood collection cannula.

As shown in FIG. 1, a blood collector 1 according to an embodiment of the present invention has a cylindrical container 2, and a columnar gasket 3. The columnar gasket 3 is slidable within the cylindrical container 2 in tight contact with the inner wall thereof.

One end 2a of the container 2 is closed, while the other end 2b thereof is open. The container 2 is made of a plastic material and, in particular, of a transparent or semitransparent plastic material which allows observation of the contents therethrough. A columnar hollow body 7 is formed at the center of the closed end 2a, and has a hole 6 which communicates with a blood collection space 5 of the container 2. A collar 9 with ribs 8 is formed around the hollow body 7 and concentric with the hole 6.

A freeze-dried blood anticoagulant mass 13 is placed extending from the hole 6 of the hollow body 7 at the one end 2a of the container 2 toward a distal end corner 2c of the container 2 so as to close the hole 6. The blood anticoagulant may be heparin salts such as heparin sodium, heparin potassium, or heparin lithium; EDTA salts such as EDTA-2Na or EDTA-2K; a citrate; a fluoride; an oxalate; a double oxalate; or the like.

The heparin salts may be conveniently used since they are nontoxic to the human body. If a sodium or potassium salt is used as a blood anticoagulant for measuring the content of $Na^+$ or $K^+$ ions, Na or K of the anticoagulant acts in the form of $Na^+$ or $K^+$ ions after being dissolved in blood, thus adversely affecting measurement precision. Therefore, other types of salts are used for measuring the content of $Na^+$ or $K^+$ ions; heparin lithium is the most preferred.

An example will now be described in which a heparin lithium mass is used as a blood anticoagulant. The heparin lithium mass 13 has dimensions such that it partially enters into the hole 6 of the hollow body 7 to close it and has a large diameter at the distal end corner 2c of the container 2. In other words, the heparin lithium mass 13 is preferably arranged in a mushroom-like shape as shown in FIG. 1. The heparin lithium mass 13 can thus provide an excellent buffer effect against blood.

Figure 3:
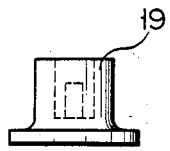
FIG. 3 is a side view of a cap which is used for forming a blood anticoagulant mass in a blood collection space of a blood collector according to the present invention.

The process for fixing the heparin lithium mass 13 at the distal end of the container 2 will be briefly described. A heparin lithium solution having a concentration of about 1,000 heparin units/ml of water is filtered using a membrane filter having a pore size of 0.45μ and is thus sterilized. After covering the top of the hollow body 7, having a volume of, for example, 2 ml and having a silicone-coated inner surface, with a cap 19 as shown in FIG. 3, 0.1 ml of the prepared heparin lithium solution is poured into the distal end of the container 2. After covering the other end 2b of the container 2 with an aluminum foil layer or the like so as to prevent the introduction of foreign materials or air during freeze-drying, the hollow body 7 containing the heparin lithium solution is placed in a freezer at a temperature of −20° C. or below for 1 hour. While maintaining the freezer at a temperature of −20° C. or below, the heparin lithium solution is freeze-dried under a reduced pressure of 0.2 Torr or less (0.2 to 0 Torr) for 5 hours. Then, the aluminum foil layer or the like is immediately removed from the other end 2b of the container, and the gasket 3 is inserted into the container 2. The obtained container 2 is inserted into an aluminum bag or the like and is heat sealed. This process is easily performed and does not require an adhesive or the like. The heparin salt mass 13 thus obtained in situ by freeze-drying is in a cotton-like form; it allows good permeation of gases such as air, and is securely fixed to the inner walls of the container 2 and the hollow body 7 defining the hole 6.

Alternatively, a freeze-dried heparin lithium mass obtained by preforming may be fixed in a predetermined position with a polymeric adhesive which may not adversely affect blood tests.

Figure 4:
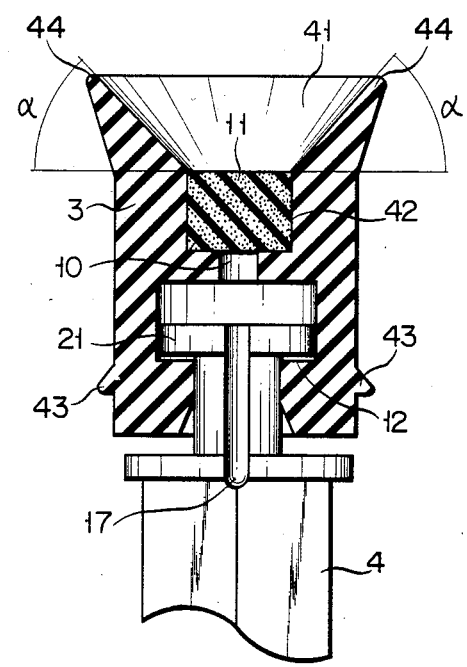
FIG. 4 is an enlarged sectional view of a gasket used in the blood collector of the present invention.

As best shown in FIG. 4, the gasket 3 has a columnar shape. In order to allow easy sliding movement of the gasket 3 within the container 2, projections 43 and 44 respectively formed at the rear and forward ends of the gasket 3 slide in tight contact with the inner wall of the container 2. A communication hole 10 is formed at the center of the gasket 3 to extend along the axial direction thereof. A recess 41 communicating with the communication hole 10 is formed at the center of the distal end of the gasket 3. A filter 11 to be described later is inserted in a filter mount portion 42 within the communication hole 10. A tapered angle α of the recess 41 is preferably 45° or more. In general, a blood collector is inclined within an angle range of 45° from the normal line to the penetrating point on a horizontally laid arm of a patient. Even if the blood collector of the present invention is used as inclined within such an angle range, air is collected in the recess 41 and is exhausted. Therefore, almost no air remains within the container.

The gasket 3 is preferably made of material having elasticity and transparency so as to allow visual observation of blood inside the transparent container 2 and the transparent gasket 3. The degree of transparency need not be complete transparency but may be semi-transparency; the transparent material need only allow the confirmation of blood level from the outside.

The elastic materials having transparency which may be used for the gasket 3 may be elastomers, examples of which will be exemplified below. Note that the elastic material need not be limited to those exemplified below but may include other elastomers and compounds thereof.

Transparent Elastomers (1) Rubber-type Elastomer

Figure 5:
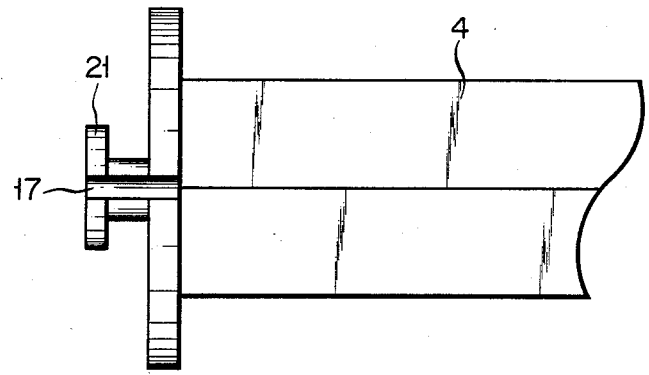
FIG. 5 is a side view showing a plunger part of the blood collector.

Transparent rubber, pure rubber, semi-translucent rubber (2) Thermoplastic Elastomer SBS-type elastomer, PVC-type elastomer, olefin-type elastomer, silicone-type elastomer, urethane-type elastomer, EVA-type elastomer, polyurethane-type elastomer, polyester-type elastomer A plunger 4 is connected to the proximal end of the gasket 3. As shown in FIGS. 5 and 6, the plunger 4 has a distal end 21 which fits inside a plunger fitting portion 12 formed at the center (inside) of the gasket 3 (FIG. 4). A communication groove 17 for communicating the communication hole 10 of the gasket 3 with the ambient air is formed on the surface of the plunger 4.

The filter 11 inserted into the filter mount portion 42 of the gasket 3 has pores and is permeable to the air and impermeable to blood. Although various materials satisfy these requirements, the filter 11 preferably comprises a sintered filter which is obtained by sintering particles of a thermoplastic polymer such as polypropylene, polyethylene, or polyacrylonitrile, from the viewpoint of ease in molding. The filter 11 preferably swells with water.

The filter 11 with such a water-swelling property may be obtained by combining a filter material with a water-swelling material. Such a water-swelling material is preferably a polymeric material which swells to a weight 100 to 1,000 times its original weight within 10 minutes upon contact with water at room temperature or body temperature. Such a water-swelling polymeric material includes various resins which absorb water well. From the viewpoint of less adverse effects on collected blood, examples of such a water-swelling polymeric material include acrylate-type starch-grafted materials such as starch-acrylonitrile, starch-acrylic acid, starch-acrylamide, starch-sodium acrylate, or the like and hydrolyzates thereof; acrylic polymers such as partially saponified polyvinyl alcohol, polyacrylate or acrylic acid-vinyl alcohol, or the like; polyethylene oxide; cellulose-type polymers and the like.

A water-swelling polymeric material selected is contained in a dry particle form in the filter. The filter preferably contains the water-swelling polymeric material in an amount of 10 to 60% by weight and preferably 10 to 40% by weight.

In order to mix the water-swelling polymeric material with the filter material, the selected polymeric material is mixed with a filter material and the mixture is sintered to obtain the filter. For example, particles of a water-swelling polymeric material are homogeneously dispersed in particles of a thermoplastic filter material as exemplified hereinabove before molding of the filter. The mixture is poured into a mold and is molded under heating and compression.

A water-swelling filter obtained in this manner swells upon contact with blood to close the hole 10 of the gasket 3 so as to prevent passage of blood therethrough.

In the blood collector of the configuration as described above, the capacity of the blood collection space 5 may be freely varied by movement of the gasket 3 upon operation of the plunger 4. However, a columnar body defining the blood collection space 5 together with the inner wall at the distal end of the container 2 is not limited to such a gasket 3 which is free to move. For example, the columnar body may be a sealing stop 18 fixed within the container 2, as shown in FIG. 7. The sealing stop 18 also has a communication hole 10, and a filter 11 as described above is arranged across the communication hole 10. The sealing stop 18 may be made of the same material as that of the gasket 3.

In practical use of the blood collector 1 of the present invention, the gasket 3 is first moved by the plunger 4 so as to form a blood collection space 5 having a suitable capacity. After mounting a hub 15 with the cannula 14 as shown in FIG. 2 on the container 2, the cannula 14 is penetrated into a blood vessel. Then, blood flows into the blood collection space 5 through the cannula 14, the hub 15 and the hole 6 of the hollow body 7 due to blood pressure. Since the heparin lithium mass 13 is fixed within the hole 6 of the columnar body and the distal end of the container, the jet current of blood under pressure is buffered by the heparin lithium mass 13 and also dissolves it. The blood is gradually collected in the blood collection space 5 and the jet current of blood will not form air bubbles in the distal end corner 2c of the container 2, the hole 6 of the hollow body 7, or the hub 15. For this reason, the filter 11 inside the gasket 3 may not be wetted before air in the blood collection space 5 is exhausted. By the time the herapin mass 13 is dissolved, blood collected in the blood collection space 5 buffers the jet current of fresh blood, thus causing no problem. The jet current of collected blood must be buffered within the initial period of blood collection. The blood collector of the present invention effectively performs such buffering so that it may not cause any problem when blood must be collected from a patient suffering from hypertension.

During blood collection, the blood level in the blood collection space 5 gradually rises; the air replaced by blood is exhausted to the outside through the filter 11 and the communication hole 10 of the gasket 3. As the air inside the blood collection space 5 is replaced by blood, blood contacts the filter 11. Then, the water-swelling polymeric material contained in the filter 11 swells upon absorption of water to seal blood in the blood collection space 5 from ambient air. Thus, blood which is treated for anticoagulant property by heparin lithium is filled in the blood collection space. Therefore, even if a jet current of blood enters the space, it is buffered by the heparin lithium mass, so that no air bubbles may be formed and air does not remain in the collected blood.

In order to demonstrate advantageous effects of a blood collector of the present invention, a control sample was prepared which did not have a heparin lithium mass fixed thereto. Blood pressure and blood flow properties of both collectors were examined under the following conditions. The obtained results are shown in Table 1.

(1) Syringe used

A syringe used was a 2-ml plastic syringe (product of Terumo) with its plunger and gasket being removed therefrom.

(2) Amount of freeze-dried heparin lithium fixed

One point one milliliter of a heparin solution having a concentration of about 1,000 units/ml of water was poured in the syringe and was freeze-dried.

(3) Inclined angle of blood collector during blood collection

45°

(4) Type of blood used

Fresh calf blood; 42% Ht value (5) Test procedures

A cannula of 20 to 23G (product of Terumo) was mounted on the syringe of item (1) above. Two hundred milliliters of calf blood with the adjusted Ht value were poured in a 200 ml blood bag (product of Terumo). Blood pressure was adjusted to 80 to 140 mmHg as shown in Table 1 below by a "MediQuick" (trade name of Terumo). The cannula of the syringe was penetrated into the inlet port of the bllod bag (with an inclined angle of 45°) under each blood pressure in Table 1 below, and blood flow properties were observed.

(6) Symbols in Table 1

H: with freeze-dried heparin lithium mass fixed

N: without freeze dried heparin lithium mass fixed (7) Evaluation method o: No jet current of blood was observed; no air remained in the hub and at the distal end corner of the syringe.

x: A jet current of blood was observed, and/or air remained in the hub or the distal end corner of the syringe.

TABLE 1

| | Blood Pressure and Blood Flow Properties | | | | | | | |
|---|---|---|---|---|---|---|---|---|
| | | Blood Pressure (mmHg) | | | | | | |
| Cannula G | Heparin | 80 | 90 | 100 | 110 | 120 | 130 | 140 |
| 20 | H | O | O | O | O | x | x | x |
| | N | O | x | x | x | x | x | x |
| 21 | H | O | O | O | O | O | x | x |
| | N | O | x | x | x | x | x | x |
| 22 | H | O | O | O | O | O | O | x |
| | N | O | O | O | x | x | x | x |
| 23 | H | O | O | O | O | O | O | O |
| | N | O | O | O | x | x | x | x |

As may be seen from Table 1 above, a jet current of blood is buffered by the heparin lithium mass fixed at the distal end portion of the container 2 in the blood collector of the example of the present invention. Therefore, air bubbles may not be formed or air may not remain in the container 2, which often occur when blood must be collected from a patient suffering from hypertension.

As may be seen from the above description, the blood collector of the present invention has the following advantages:

(1) Even if blood to be collected is under a high pressure, the flow of blood is buffered by the freeze-dried heparin lithium mass. Nor are air bubbles formed in the blood collection space, and air may not remain in the blood collection space. The water-swelling polymeric material in the filter swells at a proper time upon contact with blood, so that the air in the blood collection space before blood collection may be replaced by collected blood and exhausted to the outside. The air does not remain in the space to adversely affect blood analysis.

(2) When a blood coagulating agent is a heparin salt, it is nontoxic to the human body. Therefore, even if the collected blood with the heparin salt dissolved therein flows back into the patient's body by some accident, it will not provide any ill effects to the patient.

(3) If the heparin salt is heparin lithium, it will not have any adverse effect on measurement of $Na^+$ or $K^+$ ions in blood.

(4) If the heparin salt mass is sealed with an aluminum foil or the like, it is kept in the condition immediately after freeze drying. Therefore, the heparin salt mass has better water absorption property and dissolving property in water as compared to heparin at normal temperature or heparin dried by heating. The heparin salt mass of the present invention thus has excellent blood anticoagulating properties.

(5) If a heparin mass which is not fixed is used, it does not contact with initially introduced blood and does not provide a buffer effect depending upon the tilt angle of the syringe. However, the blood collector of the present invention is not subject to this problem.

(6) If the gasket is kept slidable, a blood collection space of desired capacity may be set by moving it.

(7) If the filter arranged in the gasket or sealing stop can swell by absorption of water, the filter swells upon contact with blood after the blood is filled in the blood collection space. The container is thus sealed from the ambient air after blood collection, providing no adverse effects to any subsequent blood analysis.

What we claim is:

1. A blood collector, comprising:
   a cylindrical body having a closed end an open end;
   a hollow body which is arranged at the closed end of said cylindrical body and which has a hole communicating with an interior of said cylindrical body; collection means for communication with the hole of said hollow body;
   a columnar body which is arranged within said cylindrical body to be in tight contact with an inner wall thereof and a distal end of which defines a blood collection space with the closed end of said cylindrical body, said columnar body having a hole which allows said blood collection space to communicate with the outside atmosphere;
   a freeze-dried blood anticoagulant mass which is secured inside said blood collection space and tightly fixed to an inner surface of the closed end of said cylindrical body to block and close the hole of said hollow body, so that jet currents of blood entering the hole of said hollow body under pressure are buffered by said mass, said mass being capable of being dissolved by the entering blood as the blood fills said blood collection space and, said mass having a permeability such that it allows gases to permeate therethrough; and
   a filter which is arranged to laterally cross the hole of said columnar body, said filter being permeable to gases and impermeable to blood at least before being brought into contact with the blood which fills said blood collection space.

2. A blood collector according to claim 1, wherein the anticoagulant mass is a heparin salt.

3. A blood collector according to claim 2, wherein the heparin salt is heparin lithium.

4. A blood collector according to claim 1, wherein the anticoagulant mass partially extends into said hole of said hollow body.

5. A blood collector according to claim 1, wherein said filter is adapted to swell upon contact with blood to seal said hole of said columnar body thereby preventing passage of blood therethrough.

6. A blood collector according to claim 5, wherein said filter comprises a sintered body of a mixture of particles of a thermoplastic polymer and of a water-swelling polymer.

7. A blood collector according to claim 1, wherein said columnar body is slidable within said cylindrical body.

8. A blood collector according to claim 7, wherein said columnar body has a plunger at a proximal end thereof.

9. A blood collector according to claim 1, wherein said columnar body is fixed within said cylindrical body.

10. A blood collector according to claim 1, wherein said mass has a mushroom-like shape.

11. A blood collector according to claim 10, wherein said mushroom-like shaped mass has a smaller diameter portion and a larger diameter portion, said smaller diameter portion at least partially entering the hole of the hollow body to close it, and the larger diameter portion being interior of the hollow body adjacent the hole.

12. A blood collector according to claim 11, wherein said hollow body has tapered walls leading to said hole, said larger diameter portion of said mass contacting said tapered walls.

13. A blood collector according to claim 1, wherein said mass partially enters the hole of the hollow body to close it, and has a large diameter portion at the portion of said cylindrical body adjacent said hole.

14. A blood collector according to claim 1, wherein said mass is a mesh-like structure.

* * * * *

UNITED STATES PATENT AND TRADEMARK OFFICE
CERTIFICATE OF CORRECTION

PATENT NO. : 4,595,021
DATED : June 17, 1986
INVENTOR(S) : A. SHIMIZU et al

It is certified that error appears in the above-identified patent and that said Letters Patent is hereby corrected as shown below:

COLUMN 6, line 34, "bllod" should read --blood--;

COLUMN 7, line 47 (claim 1), after "closed end", insert --and--.

Signed and Sealed this

Third Day of February, 1987

Attest:

DONALD J. QUIGG

*Attesting Officer*   *Commissioner of Patents and Trademarks*